US010453552B2

United States Patent
Lilley et al.

(10) Patent No.: US 10,453,552 B2
(45) Date of Patent: Oct. 22, 2019

(54) SYSTEMS AND METHODS FOR DETERMINING ATTRIBUTES OF BIOLOGICAL SAMPLES

(71) Applicant: Liquid Biosciences, Inc., Aliso Viejo, CA (US)

(72) Inventors: Patrick Lilley, Aliso Viejo, CA (US); Beau Walker, Irvine, CA (US); Michael John Colbus, Upland, CA (US)

(73) Assignee: LIQUID BIOSCIENCES, INC., Aliso Viejo, CA (US)

( * ) Notice: Subject to any disclaimer, the term of this patent is extended or adjusted under 35 U.S.C. 154(b) by 0 days.

(21) Appl. No.: 15/585,073

(22) Filed: May 2, 2017

(65) Prior Publication Data

US 2019/0155987 A1 May 23, 2019

(51) Int. Cl.
*G01N 33/48* (2006.01)
*G16B 5/00* (2019.01)

(52) U.S. Cl.
CPC ..................................... *G16B 5/00* (2019.02)

(58) Field of Classification Search
None
See application file for complete search history.

(56) References Cited

U.S. PATENT DOCUMENTS

| 4,075,475 A | 2/1978 | Risby et al. |
| 5,846,492 A | 12/1998 | Jacobs |
| 7,172,902 B2 | 2/2007 | Samsoondar |
| 2005/0064422 A1 | 3/2005 | Barnidge et al. |
| 2008/0305479 A1 | 12/2008 | Van Den Boom |
| 2009/0137063 A1 | 5/2009 | Skold et al. |

FOREIGN PATENT DOCUMENTS

WO 2013170011 A2 11/2013

OTHER PUBLICATIONS

Anton, Gabriele, et al; Pre-Analytical Sample Quality: Metabolite Ratios as an Intrinsic Marker for Prolonged Room Temperature Exposure of Serum Samples; PLOS ONE; Mar. 30, 2015.
Ellervik, Christina, et al; Preanalytical Variables Affecting the Integrity of Human Biospecimens in Biobanking; Clinical Chemistry 61:7, 914-934; 2015 American Association for Clinical Chemistry.
Kamlage, Beate; Quality Markers Addressing Preanalytical Variations of Blood and Plasma Processing Identified by Broad and Targeted Metabolite Profiling; Clinical Chemistry 60:2; 399-412; 2014 American Association for Clinical Chemistry.
Yin, Peiyuan; Preanalytical Aspects and Sample Quality Assessment in Metabolomics Studies of Human Blood; Clinical Chemistry 59:5; 1-13; Papers in Press published Feb. 5, 2013 as doi:10.1373/clinchem.2012.199257.
Yin, Peiyuan; Effects of pre-analytical processes on blood samples used in metabolomics studies; Anal Bioanal Chem (2015) 407; 4879-4892; published online Mar. 4, 2015; Springerlink.com.
International Search Report and Written Opinion, PCT/US2017/030703, dated Nov. 29, 2017.

*Primary Examiner* — Larry D Riggs, II
(74) *Attorney, Agent, or Firm* — Entralta P.C.; Justin G. Sanders; Peter D. Weinstein

(57) ABSTRACT

Systems and methods of determining pre-quantitation attributes of biological samples using post-quantitation attributes of those samples is disclosed. By altering a set of biological samples in a measurable way before running the set through an instrument (e.g., a mass spectrometer), a model can be developed that enables determination of the unknown pre-quantitation attributes in other biological samples as a function of post-quantitation attributes.

21 Claims, 4 Drawing Sheets

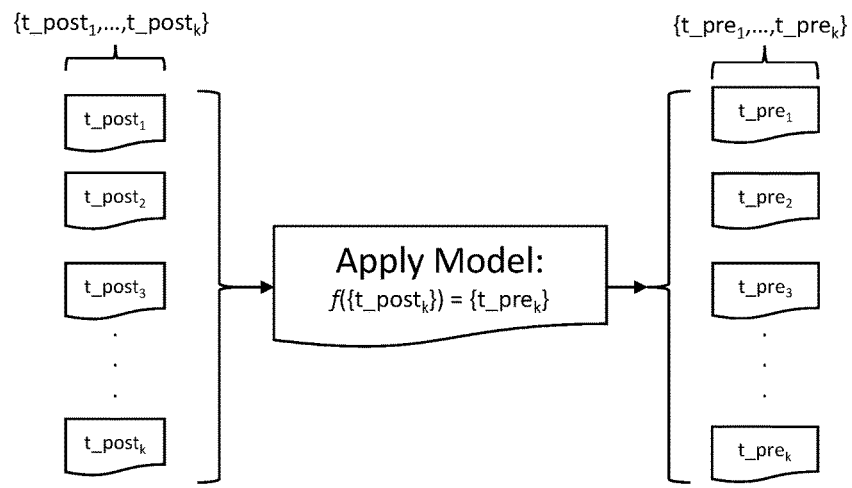
Figure 7
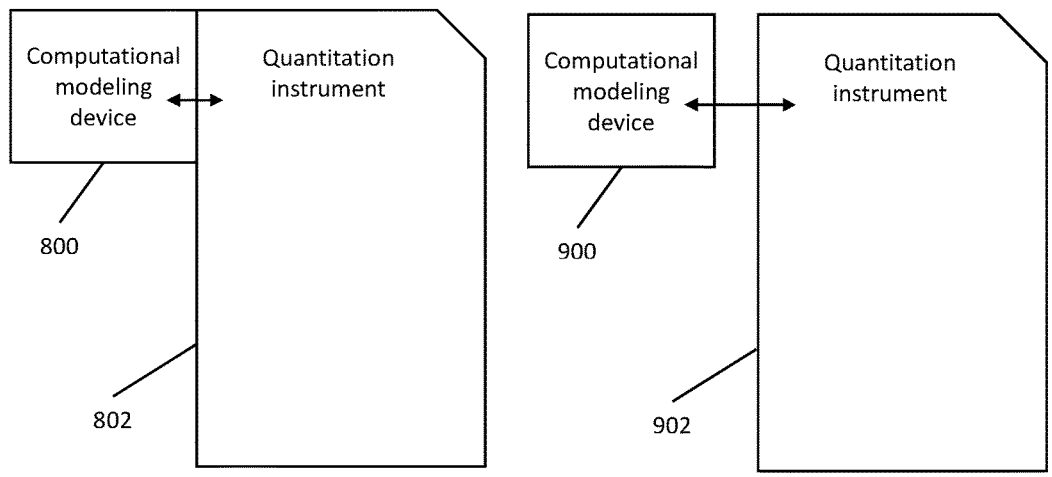
Figure 8
Figure 9

SYSTEMS AND METHODS FOR DETERMINING ATTRIBUTES OF BIOLOGICAL SAMPLES

FIELD OF THE INVENTION

The field of the invention is biological sample testing.

BACKGROUND

The background description includes information that may be useful in understanding the present invention. It is not an admission that any of the information provided in this application is prior art or relevant to the presently claimed invention, or that any publication specifically or implicitly referenced is prior art.

Quality control is a major issue in the diagnostic and laboratory testing industry, where accuracy of results is paramount to not only the efficacy of diagnostic and treatment procedures, but also to patient health. In addition to confounding results, poor sample quality can cost laboratories and researchers significantly in terms of time and money.

There are many factors that can influence sample quality. For example, mistakes or differences in the collection, storage, or preparation of biological samples can cause a sample to significantly change before it is analyzed. For example, differences in storage containers, temperature, reagents used, etc. can be detrimental to sample quality.

One solution to sample quality issues has been to increase rigor applied to pre-measurement protocols. For example, Ellervik and Vaught, in a 2015 Review Article entitled, "*Preanalytical Variables Affecting the Integrity of Human Biospecimens in Biobanking*," Clinical Chemistry 61:7 914-934 (2015), identify that pre-measurement errors account for most errors in clinical laboratory results. They propose that laboratory personnel increase the rigor of protocols and documentation surrounding pre-measurement collection and handling of biological samples as a solution for limiting diminished sample quality.

But from a practical perspective there are many situations, particularly for a commercial laboratory, where the sample history (regarding collection, handling, and preparation) is unknown, or where obtaining a higher quality sample is not possible. In these situations, additional or alternative methods must be used to determine sample quality.

U.S. Pat. No. 5,846,492 to Jacobs et al. describes a spectrophotometric method for determining sample quality measurement in the dispensing tip of an analyzer. In this method, once a patient sample is aspirated into a pipette tip, the tip can be scanned in a light-tight enclosure that will analyze the absorbance spectra of the liquid. There are many potential limitations with this approach, but notably this reference fails to appreciate advances in technology that facilitate new ways of determining sample quality.

These and all other extrinsic materials discussed in this application are incorporated by reference in their entirety. Where a definition or use of a term in an incorporated reference is inconsistent or contrary to the definition of that term provided in this application, the definition of that term provided in this application applies and the definition of that term in the reference does not apply.

Thus, there is still a need for improved systems and methods that enable determination of biological sample quality when sample history is unknown and without requiring additional equipment.

SUMMARY OF THE INVENTION

The present invention provides apparatuses, systems, and methods related to a determining an unknown pre-quantitation attribute of a target biological sample (e.g., a blood sample, a protein serum sample, a tissue sample, a CSF sample, a urine sample, and a stool sample).

In one aspect of the inventive subject matter, a method of determining an unknown pre-quantitation attribute of a target biological sample (e.g., an indication of quality of the target biological sample) is contemplated. Embodiments of the method include several steps. In one step, it requires receiving a set of biological data pairs, where each biological data pair corresponds to an altered biological sample (e.g., a deliberately degraded or incidentally degraded biological sample having a known degradation) and comprises a known pre-quantitation attribute and a set of post-quantitation attributes. In another step, it requires using the set of biological data pairs to computationally develop a model describing a relationship between post-quantitation attributes and the known pre-quantitation attribute. And in another step, it requires applying a set of target biological sample post-quantitation attributes to the model to determine the pre-quantitation attribute of the target biological sample (which is otherwise unknown).

In some embodiments, the known pre-quantitation attribute comprises a type of deliberate degradation that the altered biological sample has been subjected to. Deliberate degradation can come in the form of elapsed time, exposure to heat, exposure to cold, exposure to vibration, exposure to acceleration, exposure to ultraviolet light, exposure to exogenous substances, and exposure to other environmental forces or factors, or any combination thereof. In some embodiments, a post-quantitation attribute can include an output of results from a mass spectrometer. For example, post-quantitation attributes can include: protein quantitation, protein abundance, protein concentration, protein activity, protein presence, peptide quantitation, peptide presence, peptide abundance, RNA activity, wavelength emission measurement, and a mass to charge ratio value.

In some embodiments, the model that is computationally developed can include a plurality of models (e.g., a system of models, competing models, or an ensemble of models that work together).

In some embodiments, the step of using the set of biological data pairs to computationally develop a model additionally includes identifying and disregarding unnecessary post-quantitation attributes (e.g., not all information from a mass spectrometer will be useful in determining the unknown pre-quantitative attribute, so the unnecessary post-quantitative attributes are disregarded).

In another aspect of the inventive subject matter, a method of determining a quality of a target biological sample is contemplated. This method includes several steps. In one step, it requires receiving a set of biological data pairs, each biological data pair corresponding to an altered biological sample and comprising a known quality and a set of post-quantitation attributes. In another step, it requires using the set of biological data pairs to computationally develop a model describing a relationship between (1) a subset of post-quantitation attributes and (2) the known quality. In another step, it requires applying a set of target biological sample post-quantitation attributes to the model to determine the quality of the target biological sample.

To determine the quality of a target biological sample (e.g., a blood sample, a protein serum sample, a tissue sample, a CSF sample, a urine sample, and a stool sample), the model receives an input comprising the target biological sample post-quantitation attributes and produces an output comprising the quality of the target biological sample.

In some embodiments, the altered biological sample is degraded such that the degradation corresponds to the known quality, and the known quality can be expressed as a continuum ranging from low quality to high quality.

The type of deliberate degradation that the altered biological sample has been exposed to can be, for example, heat, cold, and/or ultraviolet light. In this method, a post-quantitation attribute can be, for example, a protein quantitation, a protein abundance, a protein concentration, a protein activity, a protein presence, a peptide quantitation, a peptide presence, a peptide abundance, an RNA activity, a wavelength emission measurement, and a mass to charge ratio value.

It is contemplated that the model can be a single model, a system of models, competing models, or an ensemble of models that work together.

In another aspect of the inventive subject matter, a system for use with an instrument is contemplated. The system develops a model to determine an unknown pre-quantitation attribute of a target biological sample. The system includes a computational modeling device communicatively coupled with the instrument. The instrument is configured to analyze altered biological samples to produce sets of post-quantitation attributes corresponding to the altered biological samples. Each altered biological sample that has been analyzed by the instrument has a corresponding biological data pair, and each biological data pair includes a known pre-quantitation attribute and a set of post-quantitation attributes.

The computational modeling device performs several functions. It receives sets of biological data pairs as input, and then it computationally develops a model describing a relationship between (1) post-quantitation attributes and (2) the known pre-quantitation attribute. The model can be applied to a set of target biological sample post-quantitation attributes to determine the unknown pre-quantitation attribute of the target biological sample.

In some embodiments, the system can be, for example, a mass spectrometer, a colorimeter, a spectrophotometer, a chromatograph, a gel electrophoresis system, a blood chemistry analyzer, a spectrofluorometer, an immunoassay system, proteomic assay systems, and an immunoturbidimetric system.

In some embodiments, the known pre-quantitation attribute is a type of deliberate degradation that the altered biological sample has been exposed to. For example, the altered biological sample can be exposed to: heat, cold, and ultraviolet light.

As with other embodiments, the model that is computationally developed can include a plurality of models (e.g., a system of models, competing models, or an ensemble of models that work together).

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWING

FIG. 7 shows a model being applied to solve for unknown pre-quantitation attributes that correspond to target biological samples.

FIG. 8 shows a system where a computational modeling device is both physically and informationally coupled with the quantitation instrument.

FIG. 9 shows a system where a computational modeling device is informationally, but not physically coupled with the quantitation instrument.

DETAILED DESCRIPTION

Figure 1:
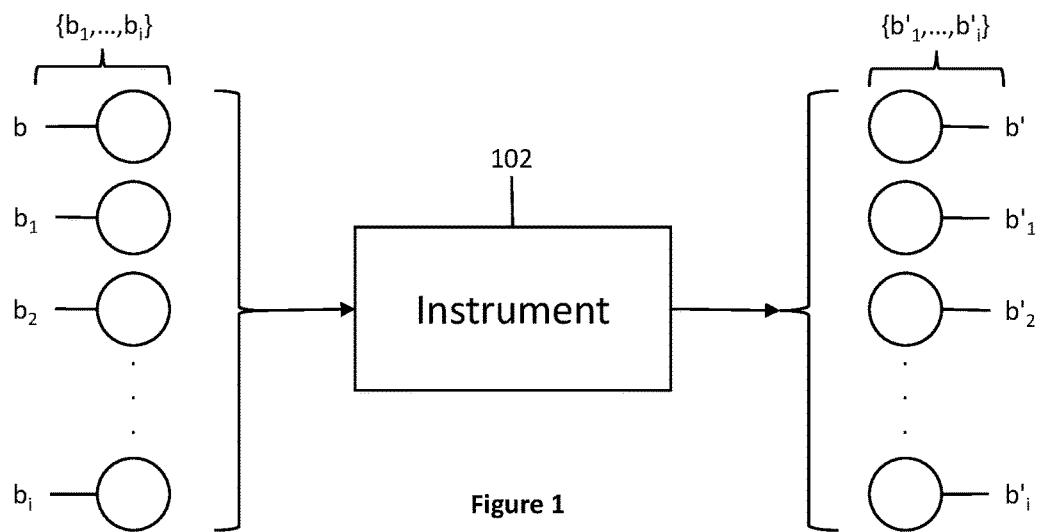
FIG. 1 shows a set of biological samples before and after analysis by an instrument.

The following discussion provides example embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

As used in the description in this application and throughout the claims that follow, the meaning of "a," "an," and "the" includes plural reference unless the context clearly dictates otherwise. Also, as used in the description in this application, the meaning of "in" includes "in" and "on" unless the context clearly dictates otherwise.

Also, as used in this application, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed considering the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements. Moreover, and unless the context dictates the contrary, all ranges set forth in this application should be interpreted as being inclusive of their endpoints and open-ended ranges should be interpreted to include only commercially practical values. Similarly, all lists of values should be considered as inclusive of intermediate values unless the context indicates the contrary.

It should be noted that any language directed to a computer should be read to include any suitable combination of computing devices, including servers, interfaces, systems, databases, agents, peers, Engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network. The following description includes information that may be useful in understanding the present invention. It is not an admission that any of the information provided in this application is prior art or relevant to the presently claimed invention, or that any publication specifically or implicitly referenced is prior art.

The systems and methods described in this application are directed to innovations related to development of models that describe relationships between known post-quantitation attributes of biological samples (e.g., attributes discovered after analyzing a biological sample using an instrument such as a mass spectrometer) and unknown pre-quantitation attributes of biological samples (e.g., an unknown metric, quality, or other attribute that is a feature of a biological sample prior to analysis by an instrument). The models described according to the inventive subject matter are developed using biological data pairs. Each biological data pair includes a known pre-quantitation attribute and a known set of post-quantitation attributes that both correspond to a biological sample.

Methods of the inventive subject matter include several steps that are discussed in more detail below. As a preliminary matter, set notation expressed as { . . . , . . . , . . . } is used in this application to express a set of items (e.g., biological samples, attributes, etc.). For example, if a set is expressed as $\{a, \ldots, a_i\}$, then the set comprises i quantity of a. Sets are sometimes also described in text instead of using set notation, and so it should be understood that even if set notation is not used, that does not preclude the possibility that a particular item could be also be expressed as a set.

When a single member of a set is referred to as, for example, $a_i$, that refers to the $i^{th}$ member of that set, where $1 \leq i \leq$ the total number of samples in the set, and i is an integer value. Prime notation is used to differentiate between biological samples that have been analyzed by an instrument and biological samples that have not. When a member of a set of biological samples is denoted as, for example, $a'_i$, that means it is a post-quantitation sample having a corresponding set of post-quantitation attributes. When making general references to sample sets, however, prime notation and non-prime notation can be used interchangeably as it still refers to the same set of biological samples.

As shown in FIG. 1, a set of biological samples is expressed as the set of samples $\{b_1, \ldots, b_i\}$. All the biological samples $\{b_1, \ldots, b_i\}$ are eventually run through an instrument 102 as shown in FIG. 1. After the biological samples $\{b_1, \ldots, b_i\}$ have been run through the instrument 102, they are notated as the set $\{b'_1, \ldots, b'_i\}$ to indicate they have been analyzed by the instrument. In this application, pre-quantitation refers to a status before a sample has been analyzed by an instrument, and post-quantitation refers to a status after a sample has been analyzed by an instrument. Thus, a pre-quantitation attribute is an attribute of a biological sample that is quantifiable prior to analysis by an instrument (e.g., quality of a biological sample), and a post-quantitation attribute is a result of analysis by an instrument (e.g., the results of an analysis). Post-quantitation attributes often come in sets, depending on the instrument used and the analysis performed.

The set of biological samples $\{b_1, \ldots, b_i\}$ can be, for example, one, or any combination of, a blood sample, a protein serum sample, a tissue sample, a cerebrospinal fluid (CSF) sample, a urine sample, and a stool sample. In some embodiments, all the samples in the set of biological samples are of the same type. In other embodiments, it is contemplated that the set of biological samples can include a variety of different types of biological samples.

In a set of biological samples that includes biological samples of different types, all the biological samples in the set are still preferably related in some manner. To be "related," the samples can, for example, have some other attribute or attributes in common. For example, a set of biological samples that includes some combination of blood samples, protein serum samples, tissue samples, CSF samples, urine samples, and stool samples, can still be used as the set of biological samples $\{b_1, \ldots, b_i\}$ as seen in FIG. 1 if the samples are related in some way outside of sample type.

"Related" biological samples could have an overlap in terms of coming from the same patient, the same hospital, the same region, the same underlying ailment, etc. It could be the case that the biological samples have other attributes in common, such as being produced by similar systems with a body (e.g., urine samples and stool samples are both excrement). In another example, if a set of biological samples includes both blood samples and tissue samples, then the biological samples in that set could be related by having the same or similar proteins, antibodies (e.g., Immunoglobulin G), cell densities, electrolytes, DNA, blood cells, etc. This same set of overlapping attributes can be applicable to many different types of biological samples, not just blood and tissue samples.

With a set of biological samples $\{b_1, \ldots, b_i\}$ and an instrument 102, the set of biological samples $\{b_1, \ldots, b_i\}$ can be analyzed (or quantitated) by the instrument 102. As mentioned above, this results in a set of post-quantitation biological samples $\{b'_1, \ldots, b'_i\}$. Instrument 102 can be a variety of instruments including: a mass spectrometer, a colorimeter, a spectrophotometer, a chromatograph, a gel electrophoresis system, a blood chemistry analyzer, a spectrofluorometer, an immunoassay system, proteomic assay systems, and an immunoturbidimetric system. Other contemplated instruments include: genomic instruments—instruments to measure gene expression of DNA, miRNA, mRNA, lncRNA, such as the Nanostring® nCounter®; genomic instruments—gene sequencers, such as Illumina® next-generation sequencers (NGS); and proteomic instruments—protein assays, such as SomaLogic® SOMAscan Assay and SDS Page instruments.

Figure 2:
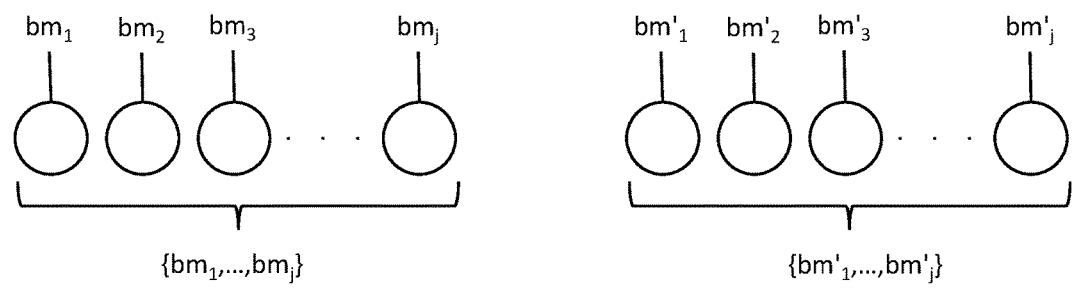
FIG. 2 shows a model-building set of biological samples before and after analysis by an instrument.

Another set of biological samples called the model-building set of biological samples is denoted as the set $\{bm_1, \ldots, bm_j\}$, as seen in FIG. 2. The model-building set of biological samples $\{bm_1, \ldots, bm_j\}$, in some embodiments, belongs to the set of biological samples $\{b_1, \ldots, b_i\}$ shown in FIG. 1. In embodiments where the model building set of biological samples $\{bm_1, \ldots, bm_j\}$ is a subset of the set of biological samples $\{b_1, \ldots, b_i\}$, then $j<i$. But in other embodiments, the model building set of biological samples $\{bm_1, \ldots, bm_j\}$ is not a subset of the set of biological samples $\{b_1, \ldots, b_i\}$. In those embodiments, it is still the case that $j<i$. This is because methods of the inventive subject matter are most useful for taking a relatively small set of model-building biological samples to create a model that enables determination of an otherwise unknown pre-quantitation attribute of biological samples belonging to the set $\{b_1, \ldots, b_i\}$.

The set of biological samples $\{b_1, \ldots, b_i\}$ can be of one or more types (as discussed above), while the model-building set of biological samples $\{bm_1, \ldots, bm_j\}$ can be of one or more types sharing no overlap in type with the set of biological samples $\{b_1, \ldots, b_i\}$. It is important for different types of biological samples used in methods of the inventive subject matter to be related. For example, a model developed using a model-building set of biological samples of one type could take into account post-quantitation attributes that also pertain to other types of biological samples. Thus, the model-building set of biological samples $\{bm_1, \ldots, bm_j\}$ does not need to be the same type of biological sample as the set of biological samples $\{b_1, \ldots, b_i\}$.

Each biological sample in the model-building set of biological samples $\{bm_1, \ldots, bm_j\}$ has a known pre-quantitation attribute (e.g., an alteration or a degradation). In some embodiments, each biological sample in the model-building set of biological samples is altered in a measurable way prior to analysis (or quantitation) by the instrument of FIG. 1. Each altered biological sample (i.e., each biological sample in the model-building set of biological samples $\{bm_1, \ldots, bm_j\}$) can be altered by, for example, deliberately degrading each biological sample.

Alteration of a biological sample (e.g., deliberate degradation or observation and measurement of incidental alterations or variances) for purposes of developing a model to determine that same alteration in other samples where that alteration is unknown has never been done before, and it is counterintuitive through the lens of current thinking. Currently, all possible precautions are taken to eliminate sample degradation, contamination, or alteration of any kind. But it has been discovered that by introducing (or measuring an existing) alteration (e.g., a degradation), that alteration can play a pivotal role in developing a model that facilitates identification of similar alterations in biological samples where the existence, absence, or degree of alteration is unknown.

In the past, it did not make sense to deliberately alter a biological sample (or use an incidentally altered biological sample where the alteration is known) because the overarching goal has always been to ensure that all samples analyzed by an instrument are already "good." "Good," in this context, could mean that the biological samples were uncontaminated, unaltered, un-degraded, or otherwise unaffected by external forces, efforts, materials, conditions, etc. In making these efforts to ensure biological samples are "good," the desire was to ensure that post-quantitation attributes—developed as a result of using an instrument to analyze the biological samples—would be as close to unaffected by unknown alterations (e.g., unknown degradations) as possible to produce the "best" post-quantitation attributes possible.

As mentioned above, an alteration of a biological sample is expressed as a pre-quantitation attribute. A pre-quantitation attribute can be, for example: identity of a person or entity that harvested the sample; a location where the sample was harvested; steps taken to process the sample prior to quantitation; or any other attribute that pertains to the sample but is not directly related to a patient outcome (e.g., diagnosis of disease, mistake in protocol, or mistake in sample acquisition such as mistake in blood draw, tissue sampling, etc.). The alteration can also be: exposure to heat; exposure to cold; exposure to ultraviolet light; exposure to chemical means; or exposure to a denaturing reagent via, for example, an acid, a base, an inorganic salt, an organic solvent (e.g., alcohol, ether, and chloroform), a cross-linking agent, a disulfide bond reducer, a chaotropic agent or any combination thereof. The alteration can also be exposure to: a biological means (e.g., enzyme activity); radiation (of any type); agitation (e.g., shaking, vibration, etc.); pressure (e.g., high or low pressure (relative to 1 atmosphere of pressure)); or a change in pressure. A pre-quantitation attribute can additionally be expressed as a set of several pre-quantitation attributes (e.g., any combination of pre-quantitation attributes discussed in this application).

It is also contemplated that a pre-quantitation attribute can be a known absence of an alteration. In other words, a known alteration (or lack thereof) is a known pre-quantitation attribute corresponding to a model-building biological sample. Thus, if a sample undergoes no alteration, then the pre-quantitation attribute simply indicates an absence of alteration.

When a set of biological samples is altered before analyzing the samples using an instrument (as mentioned above), information about that alteration can be used in model development to create a model that can use post-quantitation attributes of other biological samples to determine whether those other biological samples have undergone alteration of the same type.

While the example discussed above in relation to FIGS. 1 and 2 indicates the model-building set of biological samples $\{bm_1, \ldots, bm_j\}$ exists as a subset of the biological samples $\{b_1, \ldots, b_i\}$, it is also contemplated that the model-building set of biological samples $\{bm_1, \ldots, bm_j\}$ does not necessarily need to belong to the broader set of biological samples $\{b_1, \ldots, b_i\}$. In embodiments where the model-building set of biological samples $\{bm_1, \ldots, bm_j\}$ is not a subset of the biological samples $\{b_1, \ldots, b_i\}$, a model created using that model-building set of biological samples could nevertheless be useful for determining unknown pre-analytical attributes biological samples from the set of biological samples $\{b_1, \ldots, b_i\}$, so long as the model-building set of biological samples $\{bm_1, \ldots, bm_j\}$ are related to the set of biological samples $\{b_1, \ldots, b_i\}$. When the model-building set of biological samples $\{bm_1, \ldots, bm_j\}$ are related to the set of biological samples $\{b_1, \ldots, b_i\}$, whether a subset of the set of biological samples $\{bm_1, \ldots, bm_j\}$ or not, a model developed using the model-building set of biological samples $\{bm_1, \ldots, bm_j\}$ can still be applied to the post-quantitation attributes of the set of biological samples by virtue of that relatedness.

In preferred embodiments, the biological samples $\{b_1, \ldots, b_i\}$ and the model-building set of biological samples $\{bm_1, \ldots, bm_j\}$ are run through the same type of instrument (e.g., both sets are analyzed by a mass spectrometer—it does not need to be the exact same mass spectrometer as long as the same types of post-quantitation attributes are generated). It is contemplated that biological samples used in methods of the inventive subject matter can be run through an instrument either locally or remotely as long as the instrument generates post-quantitation attributes that are useful in model development (described in more detail below).

Biological samples could be run through the instrument in groups, in sequence, all at once, etc. This process can occur over the course of hours, days, weeks, or months—it is contemplated that there is no time limit on when the samples must be run through an instrument other than constraints affecting the biological samples themselves (e.g., shelf life). In some embodiments, the amount of time that has elapsed between collecting each member of the model-building set of biological samples and running those members through an instrument can be a pre-quantitation attribute that is used in model development.

Like the set of biological samples $\{b_1, \ldots, b_i\}$ that is run through the instrument to create a set of post-quantitation biological samples $\{b'_1, \ldots, b'_i\}$, the model-building set of biological samples $\{bm_1, \ldots, bm_j\}$ is also run through an instrument (e.g., the same instrument as the biological samples $\{b_1, \ldots, b_i\}$) to create a set of post-quantitation model-building biological samples $\{bm'_1, \ldots, bm'_j\}$, as seen in FIG. 2.

As mentioned above, running biological samples through an instrument produces what are referred to as sets of post-quantitation attributes. Post-quantitation biological samples $\{b'_1, \ldots, b'_i\}$ each have a corresponding set of post-quantitation attributes. Likewise, post-quantitation model-building biological samples $\{bm'_1, \ldots, bm'_j\}$ also each have corresponding sets of post-quantitation attributes.

Depending on the instrument, post-quantitation attributes can include, for example, a protein quantitation, a protein abundance, a protein concentration, a protein activity, a protein presence, a peptide quantitation, a peptide presence, a peptide abundance, a RNA activity, a wavelength emission measurement, and a mass to charge ratio value. Additionally, each post-quantitation attribute can itself be a set of data.

While it is contemplated that post-quantitation attributes can include results directly measured by an instrument (e.g., a mass spectrometer), it is also contemplated that post-quantitation attributes can additionally include information that is inferred from results directly measured by the instrument. For example, information not directly measured can be inferred from the raw data output by mass spectrometer (e.g., via the raw, unmatched mass to charge ratio values). In another example, after a protein is synthesized (e.g., translated from RNA) it is often modified by either the addition of small molecules or the removal of peptides. A mass spectrometer can help identify these modifications, albeit indirectly, and the presence, absence, or level of modification can be a post-quantitation attribute.

Figure 3:
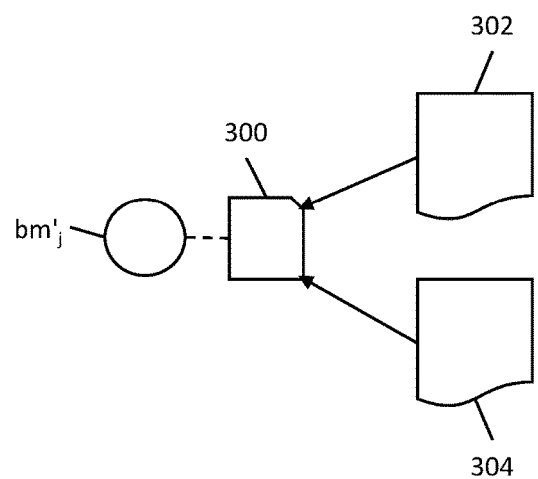
FIG. 3 shows a biological data pair corresponding to a biological sample from a model-building set of biological samples.

For a post-quantitation biological sample from the set of model-building biological samples $\{bm_1, \ldots, bm_j\}$, where a pre-quantitation attribute (e.g., an alteration or degradation) is known, a biological data pair 300 is produced, as shown in FIG. 3. Each post-quantitation biological sample $bm'_j$ therefore has a corresponding pre-quantitation attribute 302 and a set of post-quantitation attributes 304, both of which make up a biological data pair 300. Biological data pairs are unique for each post-quantitation biological sample $bm'_j$ having a known pre-quantitation attribute (e.g., biological samples belonging to the model-building set of biological samples).

Figure 4:
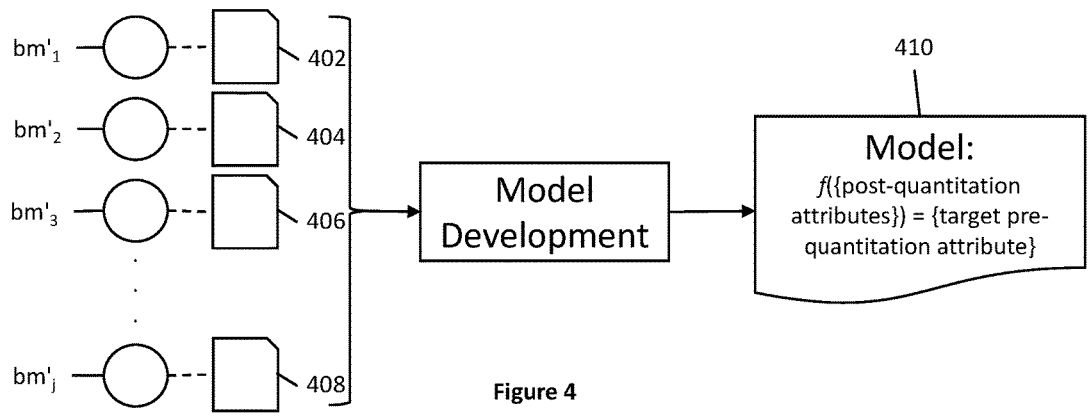
FIG. 4 shows biological data pairs used in model development to create a model.

Next, as shown in FIG. 4, biological data pairs 402, 404, 406, & 408 corresponding to each post-quantitation biological sample $bm'_j$ in the model-building set of biological samples $\{bm'_1, \ldots, bm'_j\}$ are used to develop a model 410, as shown in FIG. 4. The model 410 expresses a target pre-quantitation attribute as a function of a set of post-quantitation attributes, where the target pre-quantitation attribute that can be solved for by using the model is the same as the known pre-quantitation attributes from the biological data pairs 402, 404, 406, & 408. In some embodiments, all post-quantitation attributes from the biological data pairs 402, 404, 406, & 408 are used in model development. But in other embodiments, some post-quantitation attributes are discarded and the model is developed using only a subset of the total post-quantitation attributes. It is contemplated that model 410 can include a plurality of models (e.g., a system of models, competing models, or an ensemble of models that work together).

Figure 5:
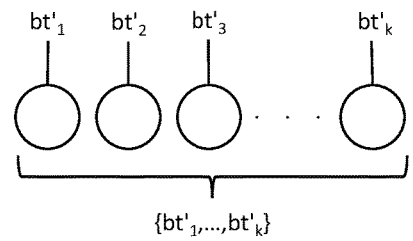
FIG. 5 shows a set of post-quantitation target biological samples.

The model 410 is developed computationally. During model development, a computer receives biological data pairs corresponding to the model-building set of biological samples as input, as shown in FIG. 4 and described above. Once the model is developed, it can be used to determine the value of unknown pre-quantitation attributes corresponding to target biological samples belonging to a set of target biological samples $\{bt'_1, \ldots, bt'_k\}$ (denoted as a "prime" set since these samples would need to be post-quantitation samples having post-quantitation attributes associated with them), as shown in FIG. 5. For example, if each biological sample $\{bm'_1, \ldots, bm'_j\}$ has a known exposure to heat, then the model would enable solving for exposure to heat in post-quantitation target biological samples $\{bt'_1, \ldots, bt'_k\}$ where that pre-quantitation attribute is unknown for each sample $bt'_k$.

Figure 6:
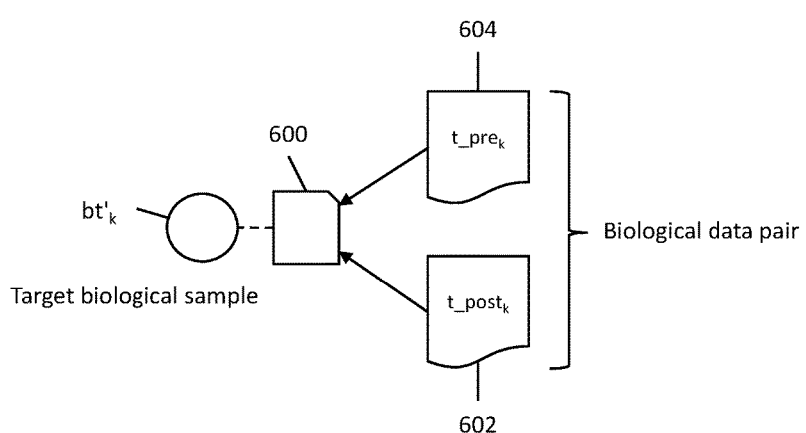
FIG. 6 shows a biological data pair of a post-quantitation target biological sample having an unknown pre-quantitation attribute.

It is contemplated that the target set of biological samples could have as few as one sample in the set, while the upper bound is theoretically unlimited. For the model to be applicable, the set of target biological samples must all have been run through the instrument that the set of model-building biological samples were run through (e.g., the same instrument or same type of instrument). After running the set of target biological samples through an instrument, each target biological sample $bt'_k$, as shown in FIG. 6, then has a corresponding biological data pair 600, where the biological data pair 600 has a known set of post-quantitation attributes 602 (also denoted as $t\_post_k$) and an unknown, target pre-quantitation attribute 604 (also denoted as $t\_pre_k$).

With a model developed using biological data pairs corresponding to post-quantitation biological samples from the post-quantitation model-building set of biological samples $\{bm_1, \ldots, bm'_j)\}$, where the model-building set of biological samples $\{bm_1, \ldots, bm_j\}$ is a subset of the set of biological samples $\{b_1, \ldots, b_i\}$, the target set of biological samples could be the members of the set of post-quantitation biological samples $\{b'_1, \ldots, b'_i\}$ minus the post-quantitation model-building set of biological samples $\{bm'_1, \ldots, bm'_j\}$. In these embodiments, the model would be easily applicable to the remaining members of the set of post-quantitation biological samples $\{'_1, \ldots, b'_i\}$ because all of the biological samples in the set of biological samples $\{b_1, \ldots, b_i\}$ are related (e.g., by type or any other "relatedness" quality mentioned above).

As mentioned above, a target set of biological samples $\{bt'_1, \ldots, bt'_k\}$ can be completely different types of biological samples than the set of biological samples $\{b'_1, \ldots, b'_i\}$, even if the target set of biological samples $\{bt'_1, \ldots, bt'_k\}$ is a subset of the post-quantitation biological samples $\{'_1, \ldots, b'_i\}$). It is also not a requirement that the target set of biological samples $\{bt'_1, \ldots, bt'_k\}$ be members of the set of biological samples.

In instances where a target biological sample is a different type of biological sample than the type (or types) of biological samples comprising the model-building set of biological samples, it can be possible for the set of post-quantitation attributes corresponding to the target biological sample to still fit into a model that has been developed using the model-building set of biological samples. Although different types of biological samples will generate different values for many post-quantitation attributes, models generated according to the inventive subject matter can be used successfully to determine target pre-quantitation attributes when the input set of post-quantitation attributes are sufficient for implementation of the model, regardless of target biological sample type.

For example, if a model is developed using a model-building set of biological samples that are all tissue samples, then the set of post-quantitation attributes that the model interprets as signaling an alteration or degradation of a tissue sample (i.e., the pre-quantitation attribute) may be the same as, or similar to, the markers of alteration or degradation (i.e., the set of post-quantitation attributes) in blood samples because many different types of biological samples, including blood samples and tissue samples, degrade in similar ways.

Thus, as shown in FIG. 7, a model developed according to the inventive subject matter can be applied to sets of post-quantitation attributes $\{t\_post_1, \ldots, t\_post_k\}$ to solve for sets of target pre-quantitation attribute solutions $\{t\_pre_1, \ldots, t\_pre_k\}$. Once solved for, the pre-quantitation attributes and sets of post-quantitation attributes can be grouped into biological data pairs corresponding to the target biological sample, expressed as $\{t\_post_k, t\_pre_k\}$.

All or some of the steps described above can also be carried out by a system that is designed for use in conjunction with an instrument (e.g., a mass spectrometer). In such systems, an electronic device can be informationally coupled with an instrument to facilitate information and data exchange. It is additionally contemplated that the electronic device can instead be implemented as software on an existing computing device (e.g., a computing device that already exists with an instrument, on a server, on a network of device or servers, etc.).

In some embodiments, like the one shown in FIG. 8, an electronic device 800 is both physically and informationally coupled with an instrument 802. In other embodiments, like the one shown in FIG. 9, the device 900 can be informationally coupled with the instrument 902, but not physically coupled with the instrument 902. In preferred embodiments, the electronic device is implemented to handle tasks such as model development and storage and manipulation of data (e.g., pre-quantitation attributes, post-quantitation attributes, biological data pairs, etc.) as necessary to facilitate implementation of methods of the inventive subject matter.

Since electronic devices of the inventive subject matter can be implemented in a virtual environment (e.g., as software), they can be implemented on, for example, a server or set of servers that are configured to exchange data with the instrument (e.g., cloud servers). Information exchange between the device and the instrument can occur via a network connection, but it can also occur by manual data exchange (e.g., transferring data using a portable data storage device such as a flash drive or portable hard drive).

Figure 10:
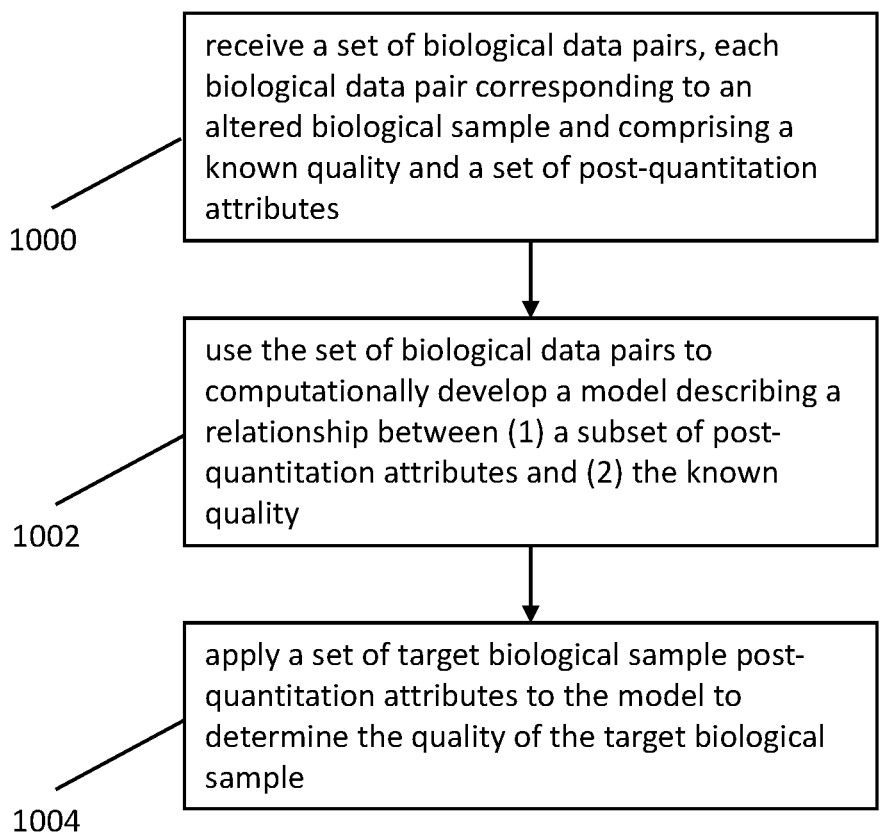
FIG. 10 is a flow chart of a method where the pre-quantitation is measure of quality.

In an example expressed in the flow chart in FIG. 10, in one step 1000, an electronic device receives a set of biological data pairs, where each biological data pair corresponds to an altered biological sample belonging to a model-building set of biological samples. Each biological data pair comprises a known quality (e.g., a quality determination based on information about the alteration of the biological sample and expressed as a pre-quantitation attribute) and a set of post-quantitation attributes (e.g., the results of analysis using an instrument). In another step 1002, the device uses the set of biological data pairs to computationally develop a model describing a relationship between (1) a subset of post-quantitation attributes (where the subset can also be the entire set) and (2) the known quality (e.g., the known pre-quantitation attribute). With the model developed, the next step 1004 is to apply a set of target biological sample post-quantitation attributes to the model to determine (e.g., solve for) the quality (e.g., the unknown pre-quantitation attribute) of each target biological sample.

An implementation of the inventive subject matter could be used in determining quality of blood serum samples belonging to a set of 1000 blood serum samples. To do this, first a set of 30 blood serum samples from 5 different healthy patients is chosen. Each sample belonging to the set of 30 is subjected to a different degradation regime, which would be recorded as degradation data (i.e., a known pre-quantitation attribute). For example, one third of the samples for each patient could be exposed to a temperature greater than 40 C, which is generally considered too high; one third could alternatively be exposed to a denaturing reagent such as alcohol; and the final one third could be reserved as controls, with no degradation.

In this example, the model-building set of biological samples with known degradation levels (i.e., known pre-quantitation attributes) is analyzed in a mass spectrometry instrument to produce output values (e.g., either the raw mass to charge values or imputed values, all of which are expressed as a set of post-quantitation attributes) which are expressed as sets of post-quantitation attributes that correspond to each blood serum sample in the model-building set.

The resulting post-quantitation attributes, along with the degradation data (i.e., the pre-quantitation attribute), would be used to generate a model, where the model would identify markers/variables from the output values (i.e., post-quantitation attributes) that correspond to/predict degradation (i.e., the pre-quantitation attribute).

A second set of biological samples (i.e., a set of target biological samples) of unknown quality can then be run through the mass spectrometry instrument. The model is then applied to the output values (i.e., the post-quantitation attributes) for this second set, and the quality level (i.e., the pre-quantitation attribute) of each of the second set of samples can be determined.

Methods of the inventive subject matter can also be useful when, for example, a medical researcher has a set of blood samples to analyze and is aware that at least one of the samples was exposed to too much heat prior to analysis by a mass spectrometer, but the researcher only knows of one or two specific samples that were exposed to this condition. The researcher could first run a biological sample from the set that they know was exposed to heat to generate a model that relates post-quantitation attributes to heat degradation, and then subsequently run all the rest of the samples with unknown qualities (e.g., unknown heat degradations)

through that model to determine which of those samples has suffered heat-related degradation.

Thus, specific apparatuses, systems, and methods have been disclosed. It should be apparent, however, to those skilled in the art that many more modifications besides those already described are possible without departing from the inventive concepts in this application. The inventive subject matter, therefore, is not to be restricted except in the spirit of the disclosure. Moreover, in interpreting the disclosure all terms should be interpreted in the broadest possible manner consistent with the context. The terms "comprises" and "comprising" should be interpreted as referring to the elements, components, or steps in a non-exclusive manner, indicating that the referenced elements, components, or steps can be present, or utilized, or combined with other elements, components, or steps that are not expressly referenced.

The invention claimed is:

1. A method of determining an unknown pre-quantitation attribute of a target biological sample using an electronic device, comprising the steps of:
   receiving, via the electronic device, a set of biological data pairs, each biological data pair corresponding to a deliberately degraded biological sample and comprising a known pre-quantitation attribute and a set of post-quantitation attributes;
   computationally developing a model, via the electronic device using the set of biological data pairs, describing a relationship between (1) a subset of post-quantitation attributes and (2) the known pre-quantitation attribute; and
   applying, via the electronic device, a set of target biological sample post-quantitation attributes to the model to determine the unknown pre-quantitation attribute of the target biological sample.

2. The method of claim 1, wherein the known pre-quantitation attribute comprises a type of deliberate degradation that the deliberately degraded biological sample has been subjected to.

3. The method of claim 2, wherein the known pre-quantitation attribute comprises at least one of exposure to heat, exposure to cold, exposure to ultraviolet light, exposure to chemical means, exposure to a denaturing reagent, exposure to an enzyme activity, exposure to radiation, exposure to agitation, exposure to pressure, and exposure to a change in pressure.

4. The method of claim 1, wherein the model comprises a plurality of models.

5. The method of claim 1, wherein the unknown pre-quantitation attribute comprises at least one of an indication of quality of the target biological sample.

6. The method of claim 1, wherein a post-quantitation attribute comprises an output of results from a mass spectrometer.

7. The method of claim 1, wherein the step of using the set of biological data pairs to computationally develop a model further comprises identifying and disregarding unnecessary post-quantitation attributes.

8. The method of claim 1, wherein the target biological sample comprises at least one of a blood sample, a protein serum sample, a tissue sample, a CSF sample, a urine sample, and a stool sample.

9. The method of claim 1, wherein a post-quantitation attribute of the set of post-quantitation attributes comprises at least one of a protein quantitation, a protein abundance, a protein concentration, a protein activity, a protein presence, a peptide quantitation, a peptide presence, a peptide abundance, an RNA activity, a wavelength emission measurement, a presence of post translational modifications, an amino acid sequence, and a mass to charge ratio value.

10. A method of determining a quality of a target biological sample using an electronic device, comprising the steps of:
    receiving, via the electronic device, a set of biological data pairs, each biological data pair corresponding to a deliberately degraded biological sample and comprising a known quality and a set of post-quantitation attributes;
    computationally developing a model, via the electronic device using the set of biological data pairs, describing a relationship between (1) a subset of post-quantitation attributes and (2) the known quality;
    applying, via the electronic device, a set of target biological sample post-quantitation attributes to the model to determine the quality of the target biological sample; and
    wherein the model, via the electronic device, receives an input comprising the target biological sample post-quantitation attributes and produces an output comprising the quality of the target biological sample.

11. The method of claim 10, wherein the deliberately degraded biological sample is degraded such that the degradation corresponds to the known quality.

12. The method of claim 10, wherein the quality comprises a continuum ranging from low quality to high quality.

13. The method of claim 10, wherein the type of deliberate degradation comprises at least one of exposure to heat, exposure to cold, exposure to ultraviolet light, exposure to chemical means, exposure to a denaturing reagent, exposure to an enzyme activity, exposure to radiation, exposure to agitation, exposure to pressure, and exposure to a change in pressure.

14. The method of claim 10, wherein the target biological sample comprises at least one of a blood sample, a protein serum sample, a tissue sample, a CSF sample, a urine sample, and a stool sample.

15. The method of claim 10, wherein a post-quantitation attribute of the set of post-quantitation attributes comprises at least one of a protein quantitation, a protein abundance, a protein concentration, a protein activity, a protein presence, a peptide quantitation, a peptide presence, a peptide abundance, an RNA activity, a wavelength emission measurement, a presence of post translational modifications, an amino acid sequence, and a mass to charge ratio value.

16. The method of claim 10, wherein the model comprises a plurality of models.

17. A system for use with an instrument, where the system develops a model to determine an unknown pre-quantitation attribute of a target biological sample, comprising:
    a computational modeling device communicatively coupled with the instrument, the instrument configured to analyze deliberately degraded biological samples to produce sets of post-quantitation attributes corresponding to the deliberately degraded biological samples;
    wherein each deliberately degraded biological sample that has been analyzed by the instrument corresponds to a biological data pair, each biological data pair comprising a known pre-quantitation attribute and a set of post-quantitation attributes;
    wherein the device:
        receives sets of biological data pairs as input, and
        computationally develops a model describing a relationship between (1) post-quantitation attributes and (2) the known pre-quantitation attribute, such that the model can be applied to a set of target biological sample post-quantitation attributes to determine the unknown pre-quantitation attribute of the target biological sample.

18. The system of claim 17, wherein the instrument is at least one of a mass spectrometer, a colorimeter, a spectrophotometer, a chromatograph, a gel electrophoresis system, a blood chemistry analyzer, a spectrofluorometer, an immunoassay system, proteomic assay systems, and an immunoturbidimetric system.

19. The method of claim 17, wherein the known pre-quantitation attribute comprises a type of deliberate degradation that the deliberately degraded biological sample has been subjected to.

20. The method of claim 17, wherein the type of deliberate degradation comprises at least one of exposure to heat, exposure to cold, exposure to ultraviolet light, exposure to chemical means, exposure to a denaturing reagent, exposure to an enzyme activity, exposure to radiation, exposure to agitation, exposure to pressure, and exposure to a change in pressure.

21. The method of claim 17, wherein the model comprises a plurality of models.

\* \* \* \* \*